(12) United States Patent
Ghun

(10) Patent No.: US 6,971,555 B1
(45) Date of Patent: Dec. 6, 2005

(54) APPARATUS FOR DISPENSING DECONTAMINATION FLUIDS

(76) Inventor: Hak Ghun, 205 Toad Rd., Durango, CO (US) 81301

(*) Notice: Subject to any disclaimer, the term of this patent is extended or adjusted under 35 U.S.C. 154(b) by 163 days.

(21) Appl. No.: 10/424,611

(22) Filed: Apr. 28, 2003

(51) Int. Cl.$^7$ .............................. B65D 83/14
(52) U.S. Cl. ..................... 222/399; 222/325
(58) Field of Search ............. 222/399, 400.7, 222/129, 132, 145.1, 325, 135, 136

(56) References Cited

U.S. PATENT DOCUMENTS

| | | | |
|---|---|---|---|
| 3,295,727 A | * | 1/1967 | Kates et al. ............ 222/136 |
| 4,979,638 A | * | 12/1990 | Bolduc ................... 222/1 |
| 5,154,320 A | * | 10/1992 | Bolduc ................... 222/129 |
| 6,675,993 B2 | * | 1/2004 | Morck .................... 222/399 |

* cited by examiner

Primary Examiner—Michael Mar
Assistant Examiner—Sonia N. Khaira
(74) Attorney, Agent, or Firm—Stites & Harbison, PLLC; John E. Vanderburgh

(57) ABSTRACT

A cartridge for assembly to the dispensing head of a Bio Cannister M-11 decontamination dispenser for maintaining booster chemicals separated from the liquid decontamination solution until ready for use thus preserving the shelf life of the decontamination system. The cartridge is configured to fit within the canister of the M-11 dispenser when assembled with the dispenser head.

6 Claims, 2 Drawing Sheets

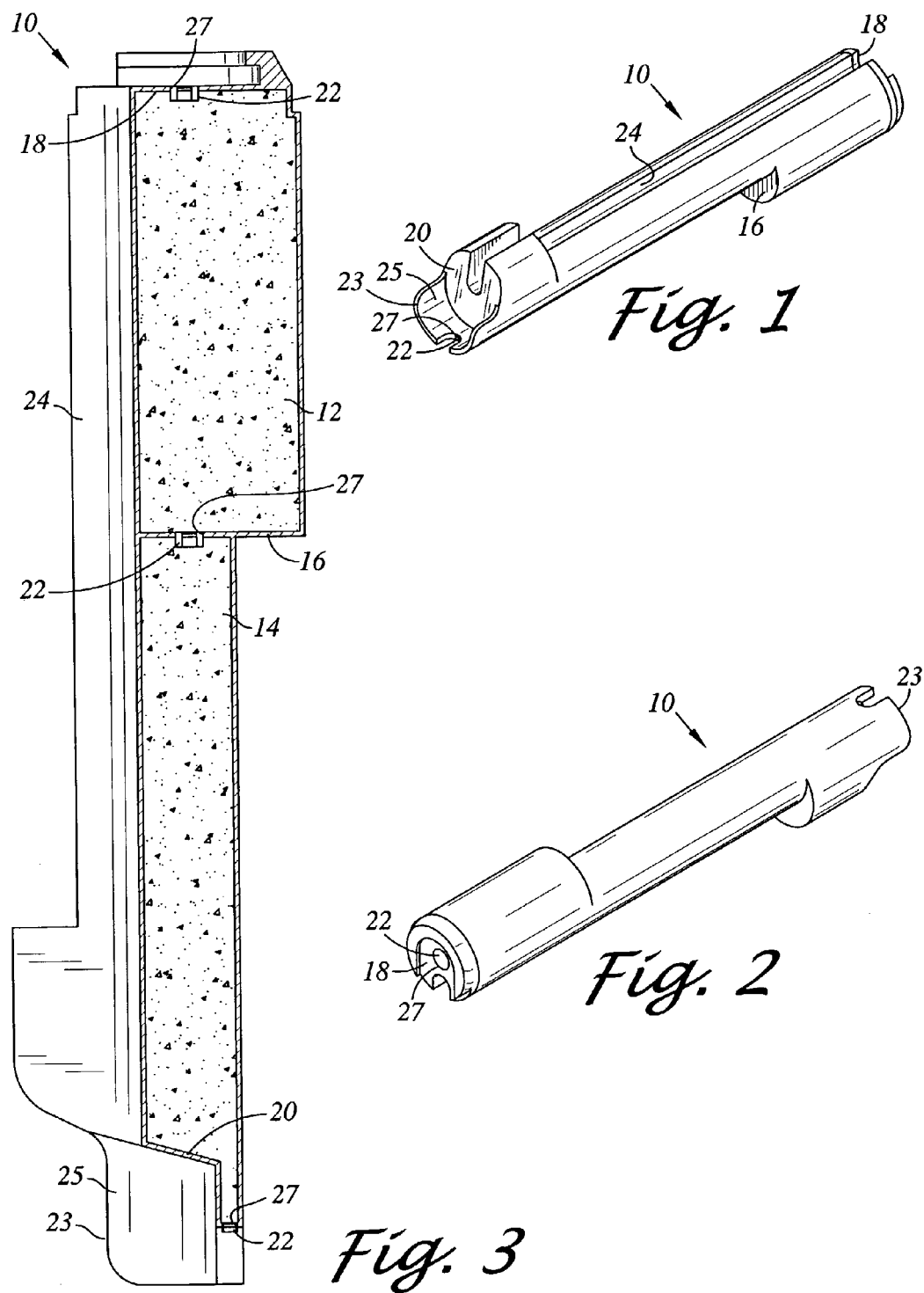

APPARATUS FOR DISPENSING DECONTAMINATION FLUIDS

FIELD OF THE INVENTION

This invention relates to apparatus for dispensing a fluid substance and more particularly, to improved decontamination apparatus in which the basic decontamination solution and the booster chemicals are maintained separately until the solution is dispensed.

BACKGROUND OF THE INVENTION

In recent times, especially since Sep. 11, 2001, there has been considerable interest in defense against chemical and biological attack. In this connection, various decontamination protocols and chemicals have been developed for the amelioration or elimination of various chemical and biological agents that are or maybe employed. Sandia National Laboratories has developed a patented broad spectrum formulation for the decontamination of areas that have been subject to chemical or biological agents. Over time, various chemical boosters have been identified for use in conjunction with the basic decontamination formulation. This formulation can be dispensed in a number of forms and by various techniques both for large areas and for small area decontamination. For small areas, a dispenser described as the Bio Canister M-11 decontamination dispenser has been in use in the decontamination of small areas and individuals. The M-11 dispenser is gas operated and comprises a dispensing head and a canister for containing the decontamination solution. Recently decontamination fluids have been improved by the admixture of booster chemicals to improve the performance of the decontamination solution. However, if boosters are to be used with the basic formulation, they must be premixed with the formulation in order to be simultaneously dispensed by the M-11 dispenser. Premixing of the booster chemicals substantially reduces the shelf life of the decontamination solution from about 10 years to 8 hours. Accordingly, premixing of booster chemicals is impractical unless the formulation and boosters are to be dispensed almost immediately.

Accordingly, it would be highly desirable to provide apparatus that permits the simultaneous dispensing of booster chemicals and basic decontamination formula through simple dispensers such as the M-11 decontamination dispenser without the attendant loss of shelf life.

SUMMARY OF THE INVENTION

The present invention comprises a hollow cartridge adapted for assembly to a dispenser for maintaining components of a chemical system separated until the system is ready to be dispensed. The cartridge includes a side wall and at least an upper and lower wall defining a compartment, each wall including a port for communication between the compartment and the exterior of the cartridge, pressure activated valves normally sealing the ports, the cartridge being adapted for assembly on the dispensing head and for being received in the canister when the canister is affixed to the dispensing head, the cartridge normally maintaining a component separate from the contents of the canister and releasing the component responsive to gas pressure for simultaneous dispensing with the contents of the canister.

In another aspect, the present invention provides apparatus for maintaining the basic decontamination formulation and the booster chemicals separate until such time as the dispenser is needed for decontamination. In this manner, the shelf life of the decontamination system, that is the basic decontamination solution and the booster chemicals, is not deleteriously affected by premixing of the chemicals and decontamination solution. Thus, the decontamination dispenser can be placed in areas ready for use in the event of chemical or biological contamination much as fire extinguishers are provided in various locations in the event of emergency. The need to premix booster chemicals and the basic formulation is eliminated resulting in the ease of use and substantial reduction in the time required to apply the decontamination system. In accordance with this aspect of the invention, the booster chemicals are stored in separate areas in a cartridge that is adapted to be received in the canister of the dispenser. The dispenser is operated by puncturing a high pressure nitrogen shell, which releases the nitrogen under pressure into the cartridge to force the booster chemicals from the cartridge into the basic decontamination solution in the canister. The high pressure gas provides a mixing action and also pressurizes the interior of the canister to dispense the now mixed decontamination system.

In another aspect of the invention, kits, including a cartridge with booster chemicals, nitrogen shells and a container of basic decontamination fluid, are provided for replenishing exhausted dispensers in the field.

BRIEF DESCRIPTION OF THE DRAWINGS

FIG. 1 is a perspective view of a cartridge adapted for the M-11 dispenser in accordance with the present invention;

FIG. 2 is a perspective view of a cartridge of FIG. 1 as viewed from the opposite side;

FIG. 3 is a side elevation partially in section of the cartridge illustrated in FIGS. 1 and 2;

DESCRIPTION OF THE PREFERRED EMBODIMENT

Figure 4:
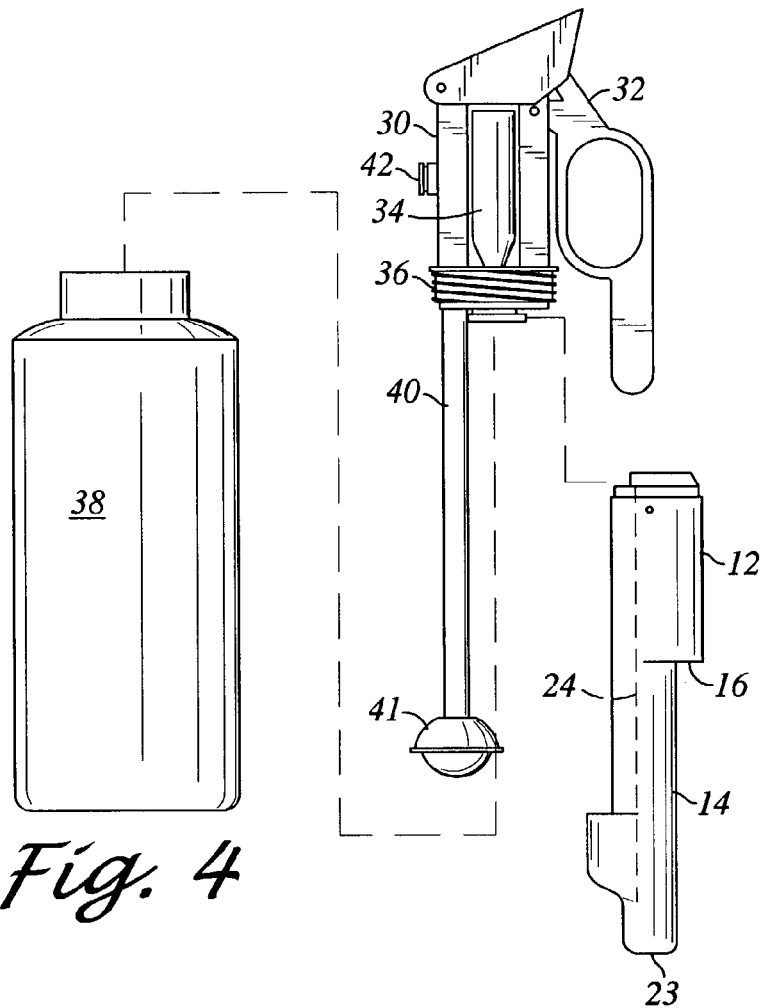
FIG. 4 is an exploded view of the M-11 dispenser and cartridge of the present invention.

Referring to FIGS. 1, 2 and 3, the cartridge of the invention, shown generally as 10, comprises a hollow cylinder, the interior of which is divided into compartments. In the embodiment shown the cartridge is divided into a first upper compartment 12 and second lower compartment 14. The compartments 12 and 14 are separated by a wall 16, and the cartridge 10 is closed at the top by a wall 18 and at the lower end by a wall 20. Openings 27 in each wall 16, 18 and 20 are normally closed by pressure-activated check valves 22 that are forced open by pressure in the cartridge to permit communication between the compartments and the exterior of the cartridge. A groove 24 open at each end extends along the length of one side of the cartridge 10. A portion 23 of the wall on the side of the cartridge 10 opposite the groove 24 is extended below the bottom wall 20 to define a cavity 25.

Figure 5:
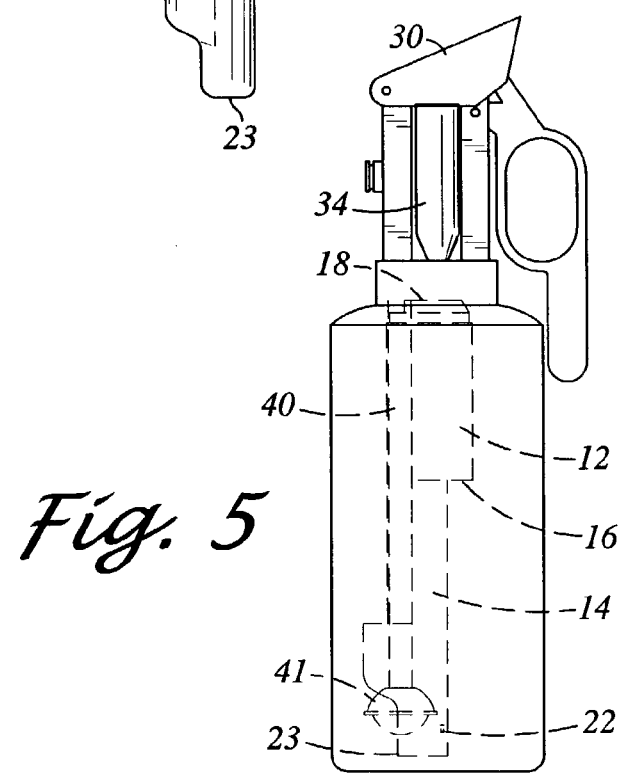
FIG. 5 is a side elevation of the M-11 dispenser in the assembled condition with the cartridge shown in phantom in the canister of the dispenser.

As is most clearly shown in FIGS. 4 and 5, the M-11 dispenser comprises a dispensing head 30 that includes a pivotally-mounted lever 32, one end of which acts against a shell 34 containing pressurized nitrogen when the lever is pivoted upwardly. The lower end 36 of the dispensing head 30 is threaded for engagement with corresponding threads (not shown) in the neck of the canister 38 that normally contains a single component decontamination fluid. The lower end 36 includes a pin (not shown) for unsealing the shell 34 when it is forced downwardly by the lever 32. A passage (not shown) extends through the lower end 36 for fluid communication between the shell 34 and the interior of the canister 38. A downwardly extending tube 40, including a filter element 41 on its lower extending end is attached to the dispensing head 30 for fluid communication with a nozzle 42.

In operation, the lever 32 is raised upwardly, causing it to act against the shell 34 forcing the end of the shell against the pin (not shown) to unseal the shell and to release the pressurized nitrogen through the cartridge 10 into the canister 38. The release of the pressurized nitrogen forces the decontamination fluid upwardly through the tube 40 and out the nozzle 42.

As mentioned, the decontamination fluid contains a single component, and the addition of booster chemicals, that improve the effectiveness of the decontamination fluid and dispensing form of the decontamination system, substantially reduce the shelf life of the decontamination fluid to a matter of hours. The cartridge 10 of the present invention contains two booster chemicals in separate compartments so that they are separated from each other and from the decontamination fluid in the canister 38.

As is most clearly shown in FIG. 5, the cartridge 10 is adapted for attachment to the decontamination head 30 and for being received in the canister 38 when so attached. More particularly, the top end of the cartridge 10 is attached to the lower end 36 of the dispensing head 30 with the check valve 22 in the top wall 18 essentially aligned with the nitrogen communication port in the lower end 36 of the dispenser head. The downwardly extending tube 40 is received in the groove 24 of the cartridge 10 and the filter element 41 is received in the cavity 25 defined by the extended portion 23 of the sidewall. As assembled, the cartridge 10 is nested around the tube 40 and the filter element 41. The assembly is no larger than the opening in the neck of the canister 38 so that the tube 40 and cartridge 10 assembly are received in the canister 38.

As described above, the operation of the dispenser 30 is initiated by raising the lever 32 to effect the opening of the shell 34 to release the pressurized nitrogen into the cartridge 10. The force of the pressurized nitrogen acts against the check valve 22 in the upper wall 18 to permit the flow of nitrogen directly into the upper compartment 12 of the cartridge 10. The pressure produced by the nitrogen on the contents of the upper compartment 12 creates sufficient pressure to open the check valve 22 in the wall 16 between the upper compartment and the lower compartment 14 which in turn forces check valve 22 in the bottom wall 20 to open, thereby providing communication through the cartridge 10 to the canister 38. The contents of both of the compartments 12 and 14 are forced into the canister 38 and are mixed therewith. The nitrogen pressure forces the mixture of decontamination fluid and booster chemicals through the filter element 41 and tube 40 for egress through the dispenser nozzle 42.

The following example is illustrative of the use of the cartridge 10 of the present invention.

EXAMPLE

An M-11 dispenser as described above was utilized to dispense a decontamination system identified as MDF-200 manufactured and distributed by Modec, Inc. under license from Sandia Laboratories, Inc. This system comprises an aqueous-based decontamination solution and aqueous solutions of hydrogen peroxide and glycol diacetate as booster chemicals. The canister 38 of the M-11 dispenser was charged with 1000 milliliters of the basic decontamination solution in liquid form. A cartridge 10 of the type described above in connection with FIGS. 1–3, was assembled onto the dispensing head 30 of the M-11 dispenser in the manner described above. The upper compartment 12 of the cartridge contained 62.4 milliliters of a 35% aqueous solution of hydrogen peroxide and the lower compartment contained 50 milliliters of a 50% aqueous solution of glycol diacetate. The dispenser head/cartridge assembly was threaded onto the canister 38 containing the decontamination solution. Upon activation of the lever unseal the shell 34 to release the pressurized nitrogen, the contents of the cartridge 10 were released into the canister 38 to catalyze the decontamination solution. The solution was dispensed indicating effective mixture of the booster chemicals with the basic decontamination solution.

In another aspect of the invention, a kit is provided to permit recharging the M-11 decontamination solution dispenser in the field for reuse. The kit comprises one or more nitrogen shells 34, a cartridge 10 containing the booster chemicals in the upper and lower compartments 12 and 14 respectively, and a container of the basic decontamination fluid.

After dispensing the decontamination system, the nitrogen shell 34 and the cartridge 10 are disassembled from the dispensing head 32 and the fresh cartridge is assembled on the dispensing head in the manner described above and a new nitrogen shell 34 is placed in the dispensing head 30. The basic decontamination fluid is placed in the canister 38 and the dispensing head/cartridge assembly is secured onto the canister. The M-11 dispenser is thus ready for reuse with the basic decontamination fluid and booster chemicals separated for maximum shelf life.

From the foregoing it can be seen that the present invention permits the M-11 dispenser to be used with the multi-component decontamination system. The decontamination system can be dispensed by the M-11 as a spray, mist, or fog, depending on the choice of nozzle employed in the dispenser head. The present invention permits a dispenser to be fully charged for immediate use without the loss of shelf life. In addition, the invention provides a kit for recharging an exhausted dispenser in the field.

While the invention has been described in connection with various embodiments, it will be understood that it may be modified by those skilled in the art without departing from the spirit and scope of the claims appended hereto.

Having defined the invention, I claim:

1. In a dispensing assembly comprising a dispensing head including a nozzle and a canister defining an interior for contents, the canister affixed to the dispensing head, a tube extending from the dispensing head into the canister for fluid communication between a liquid in the canister and the nozzle and a source of gas pressure for pressurizing the interior of the canister to force the contents through the tube for egress from the nozzle, a hollow cartridge including a side wall and at least an upper and lower wall defining a compartment, each wall including a port for communication between the compartment and the exterior of the cartridge, pressure activated valves normally sealing the ports, the cartridge being adapted for assembly on the dispensing head and for being received in the canister when the canister is affixed to the dispensing head, the cartridge normally maintaining a component separate from the contents of the canister and releasing the component responsive to gas pressure from the source for simultaneous dispensing of the component in the cartridge together with the contents of the canister.

2. The dispensing assembly of claim 1 wherein the cartridge comprises a hollow cylinder having side walls and an upper and lower end defining an interior closed at each end by a wall, an intermediate wall in the interior dividing the interior into a first upper compartment defined by the wall closing the top end, the cylinder side wall and the intermediate wall and a second lower compartment defined by the intermediate wall, the cylinder side wall and the wall closing the bottom end, each of the walls having an opening normally closed by a pressure activated valve.

3. The dispensing assembly of claim 1 wherein the cartridge is adapted for assembly on the dispensing head by a groove formed on the side wall of the cartridge that extends along the cartridge parallel to the longitudinal axis thereof.

4. The dispensing assembly of claim 2 wherein a portion of the side wall extends below the bottom wall and cooperates with the bottom wall to define a cavity for receiving a filter element carried by the free depending end of the tube when the cartridge is assembled on the dispenser head.

5. A cartridge for a Bio Canister M-11 decontamination dispenser including a dispensing head and a canister, the cartridge comprising a hollow cylinder having a side wall, an upper end adapted for connection to the dispenser and a lower end, the upper and lower ends each being normally closed by a wall to cooperate with the side wall to define an interior, a first upper compartment defined by the upper wall, the side wall and the interior wall and a second lower compartment defined by the interior wall, the side wall and the lower wall, each of the upper, interior and lower walls having an opening for communication between the upper and lower compartments and the exterior of the cartridge, pressure-activated check valves being provided in the top, interior and bottom walls normally closing the openings therein, an open ended groove extending along the length of one side of the cartridge parallel to the longitudinal axis thereof and a portion of the side wall on the side of the of the cartridge opposite the groove being extended below the bottom wall to define a cavity; whereby the cartridge is adapted to be connected to the dispensing head and to be received in the canister of the dispenser.

6. A kit for replenishing a gas operated Bio Canister M-11 decontamination dispenser comprising a hollow cylinder having a side wall, an upper end adapted for connection to the dispenser and a lower end, the upper and lower ends each being normally closed by a wall to cooperate with the side wall to define an interior, a first upper compartment defined by the upper wall, the side wall and the interior wall and a second lower compartment defined by the interior wall, the side wall and the lower wall, each of the upper, interior and lower walls having an opening for communication between the upper and lower compartments and the exterior of the cartridge, pressure-activated check valves being provided in the top, interior and bottom walls normally closing the openings therein, an open ended groove extending along the length of one side of the cartridge parallel to the longitudinal axis thereof and a portion of the side wall on the side of the of the cartridge opposite the groove being extended below the bottom wall to define a cavity, each of the compartments containing a different booster chemical, at least one shell containing compressed nitrogen and a container of decontamination solution.

* * * * *